US007781464B2

(12) United States Patent
Neogi et al.

(10) Patent No.: US 7,781,464 B2
(45) Date of Patent: *Aug. 24, 2010

(54) HETEROCYCLIC DIPHENYL ETHERS

(75) Inventors: Partha Neogi, Fremont, CA (US);
Bishwajit Nag, Union City, CA (US);
Debendranath Dey, Fremont, CA (US);
Abhijeet Nag, Fremont, CA (US);
Birendra Kumar Bhattacharya, Union City, CA (US); Vinod Kumar Singh, Sholinganallur (IN); Surendradoss Jayakumar, Sholinganallur (IN)

(73) Assignee: Bexel Pharmaceuticals, Inc., Union City, CA (US)

( * ) Notice: Subject to any disclaimer, the term of this patent is extended or adjusted under 35 U.S.C. 154(b) by 923 days.

This patent is subject to a terminal disclaimer.

(21) Appl. No.: 11/359,657

(22) Filed: Feb. 21, 2006

(65) Prior Publication Data

US 2006/0247285 A1    Nov. 2, 2006

Related U.S. Application Data

(63) Continuation-in-part of application No. 11/096,718, filed on Mar. 31, 2005, which is a continuation-in-part of application No. 10/947,047, filed on Sep. 21, 2004, now abandoned, which is a continuation of application No. 10/356,113, filed on Jan. 31, 2003, now Pat. No. 6,794,401.

(60) Provisional application No. 60/440,772, filed on Jan. 17, 2003.

(30) Foreign Application Priority Data

Feb. 17, 2005   (IN)   ........................... 347/DEL/2005

(51) Int. Cl.
A61K 31/426    (2006.01)
C07D 277/04    (2006.01)

(52) U.S. Cl. ........................... 514/369; 548/183
(58) Field of Classification Search ................. 548/100, 548/146, 183; 514/369
See application file for complete search history.

(56) References Cited

U.S. PATENT DOCUMENTS

| 5,166,137 | A | 11/1992 | Otterlei et al. |
| 5,441,971 | A | 8/1995 | Sohda et al. |
| 5,527,546 | A | 6/1996 | Penza et al. |
| 6,004,813 | A | 12/1999 | Serlupi-Crescenzi et al. |
| 6,147,100 | A | 11/2000 | Seno et al. |
| 6,316,465 | B1 | 11/2001 | Pershadsingh et al. |
| 6,331,633 | B1 | 12/2001 | Neogi et al. |
| 6,515,003 | B1 | 2/2003 | Pfahl et al. |
| 6,552,058 | B1 | 4/2003 | Sohda et al. |
| 6,562,849 | B1 | 5/2003 | Fujita et al. |
| 6,617,339 | B1 | 9/2003 | Gravestock |
| 6,620,830 | B2 | 9/2003 | Chiang |
| 6,664,281 | B1 | 12/2003 | Tajima |
| 6,667,328 | B2 | 12/2003 | Yoneda et al. |
| 6,680,387 | B2 | 1/2004 | Druzgala et al. |
| 6,686,475 | B2 | 2/2004 | Hindley |
| 6,699,896 | B1 | 3/2004 | Malamas |
| 6,706,746 | B2 | 3/2004 | Fujita et al. |
| 6,730,687 | B1 | 5/2004 | Miyachi et al. |
| 6,765,013 | B2 | 7/2004 | Pfahl et al. |
| 6,794,401 | B2 | 9/2004 | Nag et al. |
| 7,087,576 | B2 | 8/2006 | Nag et al. |
| 7,202,366 | B2 * | 4/2007 | Nag et al. .................... 548/183 |
| 2003/0229120 | A1 | 12/2003 | Olsen et al. |
| 2005/0288341 | A1 | 12/2005 | Nag et al. |

FOREIGN PATENT DOCUMENTS

| EP | 1 148 054 A1 | 10/2001 |
| EP | 1 213 287 A1 | 6/2002 |
| JP | 2001-308814 | 6/2002 |
| WO | WO 00/64888 | 2/2000 |
| WO | WO 01/02377 | 11/2001 |
| WO | WO 01/95859 | * 12/2001 ................. 548/100 |
| WO | WO 03/027081 | 4/2003 |
| WO | WO 2004/066964 | 8/2004 |
| WO | WO 2004/080480 | 9/2004 |
| WO | WO 2006/089225 | 8/2006 |

OTHER PUBLICATIONS

Morissette et al. Advanced Drug Delivery Reviews 2004, 56, 275-300.*
Vippagunta, Sudha R. "Crystalline Solids." Advanced Drug Delivery Reviews 48(2001): 3-26.*
"Tautomer." Retrieved via Internet on Oct. 24, 2008, URL: http://en.wikipedia.org/wiki/Tautomer.*
Singapore Examination Report from corresponding Singapore Application No. 200504369-0 Issued Aug. 29, 2007.
New Zealand Examination Report dated Apr. 24, 2008 for corresponding New Zealand Application No. 541328.

(Continued)

Primary Examiner—Kamal A Saeed
Assistant Examiner—Samantha L Shterengarts
(74) Attorney, Agent, or Firm—Weaver Austin Villeneuve & Sampson LLP (57) ABSTRACT

The present invention relates to novel heterocyclic diphenyl ether and diphenyl amine compounds, derivatives, analogs, tautomeric forms, stereoisomers, polymorphs, hydrates, solvates, pharmaceutically acceptable salts and pharmaceutically acceptable solvates thereof and pharmaceutically acceptable compositions containing these singly or in combination. The compounds of the present invention are effective in lowering blood glucose, serum insulin, free fatty acids, cholesterol and triglyceride levels and are useful in the treatment and/or prophylaxis of diabetes. The compounds of the present invention are effective in treatment of obesity, inflammation, autoimmune diseases such as multiple sclerosis and rheumatoid arthritis and immunological diseases, including the treatment of cancer. Furthermore, the compounds are useful for the treatment of disorders associated with insulin resistance.

11 Claims, 8 Drawing Sheets

OTHER PUBLICATIONS

Fujimoto et al., *Diabetes*, 2005, 54, 1340.
International Search Report, PCT/US2004/000790. Issued Jan. 3, 2005.
International Written Opinion, PCT/US2004/000790. Issued Jan. 3, 2005.
International Search Report, PCT/US2006/005846, Issued Jun. 22, 2006.
International Written Opinion, PCT/US2006/005846, Issued Jun. 22, 2006.
International Search Report, PCT/US04/32931, Issued Feb. 11, 2005.
International Written Opinion, PCT/US04/32931, Issued Feb. 11, 2005.
Derivative: Definition. Accessed online on Oct. 18, 2005 at http://www.answers.com/derivative. 1 pg.
Analogue: Definition. Accessed online Oct. 18, 2005 at http://www.answers.com/analogue. 1 pg.
Arend et al., Arthritis Rheum, 38:151-60,1995.
Brennan et al., Brennan et al., Inhibitory effect of TNFα Antibodies on Synovial Cell Interleukin-1 Production in Rheumatoid Arthritis, Lancet, vol. 334:244-7, 1989.
Goldenberg, Clin Ther, 21:75-87, 1999.
Haworth et al., Eur J Immunol, 21:2575-79, 1991.
Luong et al., Ann Pharmacother, 34:743-60, 2000.
Moser et al., J Clin Invest, 83:444-55,1989.
Georgian Office Action, dated Dec. 27, 2006, from corresponding U.S. Application No. PCT/US2004/000790.
China Office Action, dated Oct. 20, 2006, from corresponding U.S. Application No. PCT/US2004/000790.
Singapore Second Written Opinion, dated Mar. 9, 2007, from corresponding U.S. Application No. PCT/US2004/00790.
European Search Report from corresponding European Application No. 04701752.0 Issued Jun. 1, 2007.
International Search Report and Written Opinion Of The International Searching Authority dated Sep. 5, 2008, from related PCT Application No. PCT/US07/04007.

* cited by examiner

Fig.1 Compound 1 and 2 induces basal glucose uptake

Fig 2. Compound 1 and 2 are not cytotoxic

Fig 3. Compound 1 and 2 are not adipogenic 15 days treatment and then Oil Red O staining, Compound 1 and 2

Fig 4. Blood glucose lowering effect of Compound 2

Fig 5. Compound 2 improves oral glucose tolerance

Fig 6. Compound 1 lowers total cholesterol

Fig.7 Compound 1 and 2 inhibit TNFα levels

Fig 8. Compound 1 and 2 inhibit LPS induced NO production

HETEROCYCLIC DIPHENYL ETHERS

RELATED APPLICATIONS

This application is a continuation-in-part of application Ser. No. 11/096,718, filed Mar. 31, 2005, which claims priority pursuant to 35 USC 119 of Indian application Ser. No. 347/DEL/2005, filed Feb. 17, 2005, and which is a continuation-in-part of application Ser. No. 10/947,047, filed Sep. 21, 2004now abandoned, which is a continuation of application Ser. No. 10/356,113, filed Jan. 31, 2003, now U.S. Pat. No. 6,794,401, which claims priority pursuant to 35 USC 119(e) of provisional application Ser. No. 60/440,772, filed Jan. 17, 2003, the disclosures of which are incorporated by reference herein in their entirety.

FIELD OF THE INVENTION

The present invention relates to novel heterocyclic compounds of the general formula (I), derivatives, analogs, tautomeric forms, stereoisomers, polymorphs, hydrates, pharmaceutically acceptable salts and pharmaceutically acceptable solvates thereof, and pharmaceutically acceptable compositions containing any of these singly or in combination. The present invention more particularly provides novel compounds of the general formula (I) wherein $R_1$ through $R_7$, W, X, Y, Z and V are as defined herein:

(I)

BACKGROUND OF THE INVENTION

The causes of types I and II diabetes are not yet clear, although both genetics and environment seem to be the factors. Type I is an autonomic immune disease and patient must take insulin to survive. Type II diabetes is more common form is a metabolic disorder resulting from the body's inability to make a sufficient amount of insulin or to properly use the insulin that is produced. Insulin secretion and insulin resistance are considered the major defects, however, the precise genetic factors involved in the mechanism remain unknown.

Patients with diabetes usually have one or more of the following defects:

Less production of insulin by the pancreas;

Over secretion of glucose by the liver;

Independent of the glucose uptake by the skeletal muscles;

Defects in glucose transporters, desensitization of insulin receptors; and

Defects in the metabolic breakdown of polysaccharides.

Other than the parenteral or subcutaneous administration of insulin, there are about four classes of oral hypoglycemic agents used i.e. sulfonylurea, biguanides, alpha glucosidase inhibitors and thiazolidinediones.

Each of the current agents available for use in treatment of diabetes has certain disadvantages. Accordingly, there is a continuing interest in the identification and development of new agents, which can be orally administered, for use in the treatment of diabetes.

The thiazolidinedione class listed above has gained more widespread use in recent years for treatment of type II diabetes, exhibiting particular usefulness as insulin sensitizers to combat "insulin resistance", a condition in which the patient becomes less responsive to the effects of insulin. There is a continuing need for nontoxic, more widely effective insulin sensitizers.

Inducible nitric oxide synthase (iNOS, also termed NOS2), whose expression is regulated by IKKβ-NF-κB, is assumed to be one of the candidates that mediate inflammation-involved insulin resistance. Accumulating evidence indicates a close link between iNOS and insulin resistance. Although iNOS was originally identified in macrophages, it is now known that it is widely expressed in many tissues, including insulin-sensitive organs such as skeletal muscle, adipose tissue, and liver, in normal rodents and humans (Fujimoto et al *Diabetes*, 2005, 54, 1340). The expression of iNOS is up regulated by most, if not all, inducers of insulin resistance, including proinflammatory cytokines, obesity, free fatty acids, hyperglycemia, endotoxins, and oxidative stress. In fact, elevated expression of iNOS was observed in skeletal muscle of high-fat diet fed mice, in heart of Zucker diabetic fatty rats, and in skeletal muscle and platelets of patients with type II diabetes. Nitrosative protein modifications, such as tyrosine nitration often associated with iNOS expression, were elevated in plasma, skeletal muscle, vasculature and retina of patients with and rodent models of type II or obesity-related diabetes. Furthermore, iNOS induction resulted in attenuated insulin-stimulated glucose uptake in cultured skeletal muscle cells.

Recent advances in scientific understanding of the mediators involved in acute and chronic inflammatory diseases and cancer have led to new strategies in the search for effective therapeutics. Traditional approaches include direct target intervention such as the use of specific antibodies, receptor antagonists, or enzyme inhibitors. Recent breakthroughs in the elucidation of regulatory mechanisms involved in the transcription and translation of a variety of mediators have led to increased interest in therapeutic approaches directed at the level of gene transcription.

As indicated above, the present invention is also concerned with treatment of immunological diseases or inflammation, notably such diseases as are mediated by cytokines or cyclooxygenase. The principal elements of the immune system are macrophages or antigen-presenting cells, T cells and B cells. The role of other immune cells such as NK cells, basophils, mast cells and dendritic cells are known, but their role in primary immunologic disorders is uncertain. Macrophages are important mediators of both inflammation and providing the necessary "help" for T cell stimulation and proliferation. Most importantly macrophages make IL 1, IL 12 and TNF-α all of which are potent pro-inflammatory molecules and also provide help for T cells. In addition, activation of macrophages results in the induction of enzymes, such as cyclooxygenase II (COX-2), inducible nitric oxide synthase (iNOS) and production of free radicals capable of damaging normal cells. Many factors activate macrophages, including bacterial products, superantigens and interferon gamma (IFN γ). It is believed that phosphotyrosine kinases (PTKs) and other undefined cellular kinases are involved in the activation process.

Cytokines are molecules secreted by immune cells that are important in mediating immune responses. Cytokine production may lead to the secretion of other cytokines, altered cellular function, cell division or differentiation. Inflammation is the body's normal response to injury or infection. However, in inflammatory diseases such as rheumatoid arthritis, pathologic inflammatory processes can lead to morbidity and mortality. The cytokine tumor necrosis factor-alpha (TNF-α) plays a central role in the inflammatory response and has been targeted as a point of intervention in inflammatory disease. TNF-α is a polypeptide hormone released by activated macrophages and other cells. At low concentrations, TNF-α participates in the protective inflammatory response by activating leukocytes and promoting their migration to extravascular sites of inflammation (Moser et al., *J Clin Invest*, 83:444-55, 1989). At higher concentrations, TNF-α can act as a potent pyrogen and induce the production of other pro-inflammatory cytokines (Haworth et al., *Eur J Immunol*, 21:2575-79, 1991; Brennan et al., *Lancet*, 2:244-7, 1989). TNF-α also stimulates the synthesis of acute-phase proteins. In rheumatoid arthritis, a chronic and progressive inflammatory disease affecting about 1% of the adult U.S. population, TNF-α mediates the cytokine cascade that leads to joint damage and destruction (Arend et al., *Arthritis Rheum*, 38:151-60, 1995). Inhibitors of TNF-α, including soluble TNF receptors (etanercept) (Goldenberg, *Clin Ther*, 21:75-87, 1999) and anti-TNF-α antibody (infliximab) (Luong et al., *Ann Pharmacother*, 34:743-60, 2000), have recently been approved by the U.S. Food and Drug Administration (FDA) as agents for the treatment of rheumatoid arthritis.

Elevated levels of TNF-α have also been implicated in many other disorders and disease conditions, including cachexia, septic shock syndrome, osteoarthritis, inflammatory bowel disease such as Crohn's disease and ulcerative colitis etc.

Thus it can be seen that inhibitors of TNF-α are potentially useful in the treatment of a wide variety of diseases. While there have been prior efforts to provide compounds for inhibiting TNF-α, IL-1, IL-6, COX-2 or other agents considered responsible for immune response, inflammation or inflammatory diseases, e.g., arthritis, there still remains a need for new and improved compounds for effectively treating and inhibiting such diseases.

The TNF-α has significant role in improvement of insulin resistance. It accelerates lipolysis and increases free fatty acid levels in the circulation. It down regulates synthesis of insulin receptor, insulin receptor substrate-1(IRS-1) and glucose transporter (GLUT-4). It increases phosphorylation of IRS-1 serine-threonine and phosphortyrosine phosphatase (PTPase) activity. It inhibits insulin receptor autophosphorylation, tyrosine phosphorylation of IRS-1, PPAR-γ synthesis and insulin-stimulated glucose transport.

With an objective to develop novel compounds for lowering blood glucose, free fatty acids, cholesterol and triglyceride levels in type II diabetes and to treat autoimmune diseases such as multiple sclerosis and rheumatoid arthritis, we found that the compound 5-[4-(4-(2-amino-2-methoxycarbonyl-ethyl)phenoxy)benzyl]-thiazolidin-2,4-dione hydrochloride salt, disclosed in commonly assigned U.S. Pat. No. 6,794,401, metabolizes to {4-[4-(2,4-dioxothiazolidin-5-ylm-ethyl)-phenoxy]-phenyl}-acetic acid, which is within the scope of formula (I).

An object of the present invention is therefore to provide novel heterocyclic compounds of the general formula (I), derivatives, analogs, tautomeric forms, stereoisomers, polymorphs, hydrates, pharmaceutically acceptable salts and pharmaceutically acceptable solvates thereof, as well as pharmaceutically acceptable compositions containing any of these singly or in combination.

Another object of the present invention is to provide methods using these compounds and compositions for treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2. Mediation of cytokines such as TNFα may also provide methods of using such compounds for the treatment of cancer.

Another object of the present invention is to provide such compounds and compositions having enhanced activities, without toxic effect or with reduced toxic effect.

SUMMARY OF THE INVENTION

The present invention, relates to novel heterocyclic compounds of the general formula (I)

their analogs, their tautomeric forms, their stereoisomers, their polymorphs, their hydrates, their pharmaceutically acceptable salts, their pharmaceutically acceptable solvates, wherein ---- represents an optional bond; V represents CH or N; Y represents O or S; W represents O or $NR_8$; $R_8$ is selected from hydrogen or linear or branched, substituted or unsubstituted ($C_1$-$C_6$) alkyl groups; X represents $CR_9$, O or S wherein $R_9$ is hydrogen or $R_9$ together with Z forms a 5 or 6-membered aromatic or heteroaromatic ring system containing 1 to 2 heteroatoms selected from O, S or N; Z represents O, S or together with $R_9$ forms a 5 to 6 membered aromatic or heteroaromatic ring system containing 1 to 2 hetero atoms selected from O, S or N; $R_1$ and $R_2$ may be same or different and are independently selected from hydrogen, a halogen, hydroxy, nitro, cyano, formyl, amino, $COR_{10}$, or linear, branched, substituted or unsubstituted ($C_1$-$C_6$) alkyl group; or substituted or unsubstituted ($C_1$-$C_6$) alkoxy group; $R_{10}$ represents —$OR_{11}$ or $NR_{12}R_{13}$; where $R_{11}$ represents hydrogen, a substituted or unsubstituted group selected from alkyl, alkenyl, aryl, aralkyl, heteroaryl, or a counter ion; $R_{12}$ and $R_{13}$ may be same or different and independently represent H or substituted or unsubstituted alkyl, alkenyl or aryl groups; or $R_{12}$ and $R_{13}$ together form a heteroaliphatic or heteroaromatic ring; $R_3$, $R_4$, $R_5$ and $R_6$, are selected from hydrogen, halogen; hydroxy, nitro, cyano, formyl, amino, linear or branched, substituted or unsubstituted ($C_1$-$C_6$) alkyl or alkoxy groups; haloalkyl groups, carboxylic acid and its derivatives; substituted or unsubstituted ($C_1$-$C_6$) alkoxy groups; thiol, thioalkyl, substituted or unsubstituted sulfonamide, sulfonyl methyl group; $R_7$ represents hydrogen, substituted or unsubstituted alkyl, alkenyl, —$CH_2COOR$, aryl groups, or a counter ion; where R represents H or ($C_1$-$C_6$) alkyl group.

A useful class of compounds includes those of the formula (I) wherein Y is O; X is S or $CR_9$; $R_1$ is $COR_{10}$ and $R_2$ is hydrogen or alkyl. A particular subclass of this class includes those compounds wherein $R_3$ is hydrogen or halo; $R_4$ and $R_6$ are hydrogen; $R_5$ is hydrogen, halo, haloalkyl or alkoxy; and $R_7$ is hydrogen, —$CH_2COOR$ or a counterion.

Another useful subclass of compounds of the formula (I) includes those wherein V is CH; X is S; Y, Z and W are O; $R_{10}$ is —$OR_{11}$; $R_{11}$ is hydrogen or a counterion; $R_2$, $R_3$, $R_4$, $R_5$ and $R_6$ are hydrogen; and $R_7$ is hydrogen or a counterion.

A useful class of pharmaceutically acceptable salts of the compounds according to formula (I) includes the hydrochloride, hydrobromide, sulfate, besylate, sodium, potassium, calcium and magnesium salts.

Pharmaceutical compositions are provided by the invention comprising a therapeutically effective amount of a compound or a mixture of compounds, analogs, tautomeric forms, stereoisomers, polymorphs, pharmaceutically acceptable salts or pharmaceutically acceptable solvates thereof according to formula (I) sufficient to reduce in a subject the plasma level of glucose, fatty acids, cholesterol or triglycerides and a pharmaceutically acceptable carrier, diluent, excipient or solvate.

Pharmaceutical compositions are further provided comprising a therapeutically effective amount of a compound or a mixture of compounds, analogs, tautomeric forms, stereoisomers, polymorphs, pharmaceutically acceptable salts or pharmaceutically acceptable solvates thereof according to formula (I) sufficient to treat obesity, autoimmune diseases, inflammation, immunological diseases, diabetes or disorders associated with insulin resistance in a subject.

The pharmaceutical compositions are preferable for oral use in the form of a tablet, capsule, powder, syrup, aerosol or suspension.

Methods are provided for treating diabetes, obesity, autoimmune diseases, inflammation and immunological disease, including the treatment of cancer, comprising administering an effective amount of a compound or a mixture of compounds, analogs, tautomeric forms, stereoisomers, polymorphs, hydrates, pharmaceutically acceptable salts or pharmaceutically acceptable solvates thereof of formula (I) to a patient in need thereof.

Methods are provided for reducing the glucose, free fatty acid, cholesterol and triglyceride levels in the plasma comprising administering an effective amount of a compound or a mixture of compounds, analogs, tautomeric forms, stereoisomers, polymorphs, hydrates, pharmaceutically acceptable salts or pharmaceutically acceptable solvates thereof of formula (I) to a patient in need thereof.

A method is provided for treating the disorders associated with insulin resistance comprising administering an effective amount of a compound or a mixture of compounds, analogs, tautomeric forms, stereoisomers, polymorphs, hydrates, pharmaceutically acceptable salts or pharmaceutically acceptable solvates thereof of formula (I) to a patient in need thereof.

DETAILED DESCRIPTION OF THE INVENTION

The term analog includes a compound that differs from the parent structure by one or more C, N, O or S atoms. Hence, in a compound in which one of the N atoms in the parent structure is replaced by an S atom, the latter compound is an analog of the former.

The term stereoisomer includes isomers that differ from one another in the way the atoms are arranged in space, but whose chemical formulas and structures are otherwise identical. Stereoisomers include enantiomers and diastereoisomers.

The term tautomer includes readily interconvertible isomeric forms of a compound in equilibrium. The enol-keto tautomerism is an example.

The term polymorph includes crystallographically distinct forms of compounds with chemically identical structures.

The term pharmaceutically acceptable solvates includes combinations of solvent molecules with molecules or ions of the solute compound.

The term substituted means that one or more hydrogen atoms are replaced by a substituent including, but not limited to, alkyl, alkoxy, alkylenedioxy, amino, amidino, aryl, aralkyl (e.g., benzyl), aryloxy (e.g., phenoxy), aralkoxy (e.g., benzyloxy), carboalkoxy (e.g., acyloxy), carboxyalkyl (e.g., esters), carboxamido, aminocarbonyl, cyano, carbonyl, halo, hydroxyl, heteroaryl, heteroaralkyl, heteroaryloxy, heteroaralkoxy, nitro, sulfanyl, sulfinyl, sulfonyl, and thio. In addition, the substituent may be substituted.

The term derivative refers to a compound obtained from a compound according to Formula (I), an analog, tautomeric form, stereoisomer, polymorph, hydrate, pharmaceutically acceptable salt or pharmaceutically acceptable solvate thereof, by a simple chemical process converting one or more functional groups, such as, by oxidation, hydrogenation, alkylation, esterification, halogenation, and the like.

Suitable groups represented by $R_8$ is selected from hydrogen, linear or branched, substituted or unsubstituted ($C_1$-$C_6$) alkyl groups such as methyl, ethyl, propyl, isopropyl, n-butyl, isobutyl, t-butyl, and the like; X represents $CR_9$, O or S wherein $R_9$ is hydrogen or $R_9$ together with Z forms a 5 or 6-membered aromatic or heteroaromatic ring system containing 1 to 2 heteroatoms selected from O, S or N; Z represents O, S or together with $R_9$ forms a 5 or 6 membered aromatic or heteroaromatic ring system, containing 1 or 2 hetero atoms selected from O, S or N; $R_1$ and $R_2$ are selected from hydrogen, halogens such as fluorine, chlorine, bromine or iodine; hydroxy, nitro, cyano, formyl, amino, $COR_{10}$, linear or branched, substituted or unsubstituted ($C_1$-$C_6$) alkyl groups such as methyl, ethyl, propyl, isopropyl, n-butyl, isobutyl, t-butyl, and the like; substituted or unsubstituted ($C_1$-$C_6$) alkoxy groups such as methoxy, ethoxy, propoxy, butoxy and the like; $R_{10}$ represents —$OR_{11}$ or $NR_{12}R_{13}$; where $R_{11}$ represents hydrogen, substituted or unsubstituted ($C_1$-$C_6$) alkyl groups such as methyl, ethyl, propyl, isopropyl, n-butyl, isobutyl, t-butyl, and the like; ($C_2$-$C_{20}$) alkenyl groups such as ethenyl, propenyl, butenyl and the like which may be substituted; aryl groups, including 5 to 14-membered mono-, bi- or tricyclic ring systems, such as phenyl, naphthyl and the like which may be substituted, aralkyl groups such as benzyl, phenyl ethyl, phenyl propyl and the like, heteroaryl groups, including 5 to 14-membered mono-, bi- or tricyclic ring systems, such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like, which may be substituted; or a counter ion such as sodium, potassium or magnesium; $R_{12}$ and $R_{13}$ may be same or different and independently represent H, substituted or unsubstituted ($C_1$-$C_6$) alkyl groups such as methyl, ethyl, propyl, isopropyl, n-butyl, isobutyl, t-butyl, and the like; ($C_2$-$C_{20}$) alkenyl groups such as ethenyl, propenyl, butenyl and the like which may be substituted; aryl groups such as phenyl, naphthyl and the like which may be substituted; or $R_{12}$ and $R_{13}$ together form a heteroaliphatic or heteroaromatic ring, such as a morpholinyl, piperidinyl, piperazinyl, pyrrolidinyl, azetidinyl ring, and the like; $R_3$, $R_4$, $R_5$ and $R_6$, are selected from hydrogen, halogens such as fluorine, chlorine, bromine or iodine; hydroxy, nitro, cyano, formyl, amino, linear or branched, substituted or unsubstituted ($C_1$-$C_6$) alkyl alkoxy groups such as methyl, methoxy, ethyl, ethoxy, propyl, isopropyl, n-butyl, isobutyl, t-butyl, and the like; ($C_1$-$C_6$) haloalkyl groups such as chloromethyl, chloroethyl, trifluoromethyl, trifluoroethyl, dichloromethyl, dichloroethyl, trichloromethyl, difluoromethyl, and the like, which may be substituted; carboxylic acid and its derivatives which may be substituted, substituted or unsubstituted ($C_1$-$C_6$) alkoxy groups such as methoxy, ethoxy, propoxy, butoxy and the like; thiol, thioalkyl groups which may be substituted, substituted or unsubstituted sulfonamide and sulfonyl methyl group; $R_7$ represents hydrogen, substituted or unsubstituted ($C_1$-$C_6$) alkyl groups such as methyl, ethyl, propyl, isopropyl, n-butyl, isobutyl, t-butyl, and the like; ($C_2$-$C_{20}$) alkenyl groups such as ethenyl, propenyl, butenyl and the like which may substituted; aryl groups, including 5 to 14-membered mono-, bi- or tricyclic ring systems such as phenyl, naphthyl and the like which may substituted, —$CH_2COOR$, or a counter ion; where R represents H or ($C_1$-$C_6$) alkyl groups which may substituted.

When the groups $R_3$, $R_4$, $R_5$, $R_6$, and $R_7$ are substituted, the substituents may be selected from halogen, hydroxy, nitro, cyano, azido, amino, hydrazine, alkyl, aryl, cycloalkyl, alkoxy, aryloxy, acyl, haloacyl, acyloxyacyl, heterocyclyl, heteroaryl, monoalkylamino, dialkylamino, acylamino, alkoxycarbonyl, aryloxycarbonyl, alkoxycarbonyloxyalkyl, aryloxycarbonyloxyalkyl, cycloalkoxycarbonyloxyalkyl, alkanoyloxyalkyl, cycloalkanoyloxyalkyl alkylsulfonyl, arylsulfonyl, alkylsulfinyl, arylsulfinyl, alkylthio, arylthio, sulfamoyl, alkoxyalkyl groups or carboxylic acids and its derivatives.

A useful class of compounds includes those of the Formula (I) wherein Y is O; X is S or $CR_9$; $R_1$ is $COR_{10}$ and $R_2$ is hydrogen or alkyl. A particular subclass of this class includes those compounds wherein $R_3$ is hydrogen or halo; $R_4$ and $R_6$ are hydrogen; $R_5$ is hydrogen, halo, haloalkyl or alkoxy; and $R_7$ is hydrogen, —$CH_2COOR$ or a counterion.

Another useful subclass of compounds of the Formula (I) includes those wherein V is CH; X is S; Y, Z and W are O; $R_{10}$ is —$OR_{11}$; $R_{11}$ is hydrogen or a counterion; $R_2$, $R_3$, $R_4$, $R_5$ and $R_6$ are hydrogen; and $R_7$ is hydrogen or a counterion.

The compounds of the present invention are effective in lowering blood glucose, serum insulin, free fatty acids, cholesterol and triglyceride levels and are useful in the treatment and/or prophylaxis of type II diabetes. The compounds of the present invention are effective in treatment of obesity, inflammation, autoimmune diseases such as multiple sclerosis and rheumatoid arthritis. Surprisingly, these compounds increase the leptin level and have no liver toxicity.

Furthermore, the compounds of the present invention are useful for the treatment of disorders associated with insulin resistance, such as polycystic ovary syndrome, as well as hyperlipidemia, coronary artery disease and peripheral vascular disease, and for the treatment of inflammation and immunological diseases, particularly those mediated by cytokines such as TNF-α, IL-1, IL-6, IL-1β and cyclooxygenase such as COX-2, to include the treatment of cancer. The compounds of this class are also useful for the treatment of diabetes complications like retinopathy, neuropathy, and nephropathy and like.

The term pharmaceutically acceptable salts forming part of this invention includes base addition salts such as alkali metal salts like Li, Na, and K salts, alkaline earth metal salts like Ca and Mg salts, salts of organic bases such as lysine, arginine, guanidine, diethanolamine, choline and the like, ammonium or substituted ammonium salts. Salts may include acid addition salts which are sulphates, nitrates, phosphates, perchlorates, borates, hydrohalides, acetates, tartrates, maleates, citrates, succinates, palmoates, methanesulphonates, benzoates, salicylates, hydroxynaphthoates, benzenesulfonates, ascorbates, glycerophosphates, ketoglutarates and the like. A preferred class of salts includes the hydrochloride, hydrobromide, sulfate, besylate, sodium, potassium, calcium and magnesium salts. Pharmaceutically acceptable solvates may be hydrates or comprising other solvents of crystallization such as alcohols. The present invention provides a pharmaceutical composition, containing the compounds of the general formula (I) as defined above, derivatives, analogs, tautomeric forms, stereoisomers, polymorphs, hydrates, pharmaceutically acceptable salts and pharmaceutically acceptable solvates singly or in combination, in combination with the usual pharmaceutically employed carriers, diluents and the like, useful for the treatment of obesity, autoimmune diseases, inflammation, immunological diseases, diabetes or disorders associated with insulin resistance in a subject.

The pharmaceutical compositions may be in the forms normally employed, such as tablets, capsules, powders, syrups, solutions, aerosols, suspensions and the like; may contain flavoring agents, sweeteners etc. in suitable solid or liquid carriers or diluents, or in suitable sterile media to form injectable solutions or suspensions. Such compositions typically contain from 1 to 20% preferably 1 to 10% by weight of active compound, the remainder of the composition being pharmaceutically acceptable carriers, diluents or solvents. The preferred compositions for oral administration are in the form of a tablet, capsule, powder, syrup, aerosol or suspension.

The terms "pharmaceutically acceptable carrier (diluent, excipient or solvent)" include any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "therapeutically effective amount" or "effective amount" refers to that amount of a compound that is sufficient to effect treatment, as defined below, when administered to a mammal including humans, in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;

b) inhibiting the disease, that is, slowing or arresting the development of clinical symptoms; and/or c) relieving the disease, that is, causing the regression of clinical symptoms.

Useful compounds according to the present invention include:

1. {4-[4-(2,4-Dioxo-thiazolidin-5-ylmethyl)-phenoxy]-phenyl}-acetic acid;
2. {4-[4-(2,4-Dioxo-thiazolidin-5-ylmethyl)-phenoxy]-phenyl}-acetic acid disodium salt;
3. {4-[4-(4-Oxo-2-thioxo-thiazolidin-5-ylmethyl)-phenoxy]-phenyl}-acetic acid;
4. {4-[4-(3-Carboxymethyl-4-oxo-2-thioxo-thiazolidin-5-ylmethyl)-phenoxy]-phenyl}-acetic acid;
5. {4-[4-(2,4-Dioxo-thiazolidin-5-ylmethyl)-2-fluoro-phenoxy]-phenyl}-acetic acid;
6. {4-[2-Chloro-4-(2,4-dioxo-thiazolidin-5-ylmethyl)-phenoxy]-phenyl}-acetic acid;
7. {4-[4-(2,4-Dioxo-thiazolidin-5-ylmethyl)-2-trifluoromethyl-phenoxy]-phenyl}-acetic acid;
8. {4-[4-(2,4-Dioxo-thiazolidin-5-ylmethyl)-2-methoxy-phenoxy]-phenyl}-acetic acid;
9. {4-[4-(2,4-Dioxo-thiazolidin-5-ylmethyl)-3-fluoro-phenoxy]-phenyl}-acetic acid;
10. {4-[4-(2,4-Dioxo-thiazolidin-5-ylidenemethyl)-phenoxy]-phenyl}-acetic acid;
11. {4-[4-(2,4-Dioxo-thiazolidin-5-ylidenemethyl)-2-trifluoromethyl-phenoxy]-phenyl}-acetic acid;
12. {4-[4-(4-Oxo-2-thioxo-thiazolidin-5-ylmethyl)-2-trifluoromethyl-phenoxy]-phenyl}-acetic acid;
13. {4-[4-(4-Oxo-2-thioxo-thiazolidin-5-ylidenemethyl)-phenoxy]-phenyl}-acetic acid;
14. {4-[4-(3-Carboxymethyl-4-oxo-2-thioxo-thiazolidin-5-ylidenemethyl)-phenoxy]-phenyl}-acetic acid;
15. {4-[4-(3-Carboxymethyl-4-oxo-2-thioxo-thiazolidin-5-ylmethyl)-3-fluoro-phenoxy]-phenyl}-acetic acid;
16. {6-[4-(2,4-Dioxo-thiazolidin-5-ylmethyl)-phenoxy]-pyridin-3-yl}-acetic acid;
17. {6-[4-(4-Oxo-2-thioxo-thiazolidin-5-ylmethyl)-phenoxy]-pyridin-3-yl}-acetic acid;
18. {6-[4-(3-Carboxymethyl-4-oxo-2-thioxo-thiazolidin-5-ylmethyl)-phenoxy]-pyridin-3-yl}-acetic acid;
19. {6-[4-(2-Oxo-2,3-dihydro-1H-indol-3-ylmethyl)-phenoxy]-pyridin-3-yl}-acetic acid;
20. {6-[4-(2-Oxo-2,3-dihydro-1H-indol-3-ylmethyl)-2-trifluoromethyl-phenoxy]-pyridin-3-yl}-acetic acid;
21. {4-[4-(2-Oxo-2,3-dihydro-1H-indol-3-ylmethyl)-2-trifluoromethyl-phenoxy]-phenyl}-acetic acid;
22. {4-[4-(2,4-Dioxo-thiazolidin-5-ylmethyl)-phenoxy]-2-fluoro-phenyl}-acetic acid;
23. 2-{4-[4-(2,4-Dioxo-thiazolidin-5-ylmethyl)-phenoxy]-phenyl}-N,N-dimethyl-acetamide;
24. 2-{4-[4-(2,4-Dioxo-thiazolidin-5-ylmethyl)-phenoxy]-phenyl}-acetamide;
25. 5-{4-[4-(2-Oxo-2-piperazin-1-yl-ethyl)-phenoxy]-benzyl}-thiazolidine-2,4-dione;
26. 5-{4-[4-(2-Morpholin-4-yl-2-oxo-ethyl)-phenoxy]-benzyl}-thiazolidine-2,4-dione;
27. 2-{4-[4-(2,4-Dioxo-thiazolidin-5-ylmethyl)-phenoxy]-phenyl}-butyric acid;
28. (4-{[4-(2,4-Dioxo-thiazolidin-5-ylmethyl)-phenyl]-methyl-amino}-phenyl)-acetic acid; and
29. 5-{4-[4-(2-Oxo-2-piperazin-1-yl-ethyl)-phenoxy]-3-trifluoromethyl-benzyl}-thiazolidine-2,4-dione.

According to another feature of the present invention, there is provided a process for the preparation of the compounds of general formula (I).

General Scheme

-continued (I)

The reactions described in the processes outlined above are preferably performed by using the methods described herein:

Step-I:

The reaction of compound of formula (Ia) with 4-fluorobenzaldehyde to produce a compound of the formula (Ib) may be carried out in the presence of solvents such as tetrahydrofuran, dimethylformamide, dimethyl sulfoxide, DME and the like or a mixtures of solvents may be used. The reaction may be carried out in an inert atmosphere. The reaction may be effected in the presence of a base such as $K_2CO_3$, $Na_2CO_3$, potassium tert-butoxide, NaH or mixtures thereof. The reaction temperature may range from 60° C. to 100° C., preferably at a temperature in the range of 80° C. to 100° C. The duration of the reaction may range from 1 to 24 hours, preferably from 15 to 20 hours.

Step-II:

The reaction of the compound of the formula (Ib) with a compound of formula (Ic) is carried out in the presence of base and in the presence of a solvent such as toluene, methoxyethanol or mixtures thereof to yield a compound of formula (I). The reaction temperature may range from 60° C. to 180° C. Suitable catalyst such as piperidinium acetate or benzoate, sodium acetate or mixtures of catalysts may also be employed. The water produced in the reaction may be removed by using Dean Stark water separator or by using water-absorbing agents like molecular sieves.

Step-III:

In another embodiment of the present invention, there is provided a process for the preparation of compounds of formula (I), by reducing the penultimate step of formula (I) wherein --- represents bond. The reduction step is not required when -------- represent no bond and all other symbols are as defined earlier. The reduction of the compound of formula (I), to produce the general compound of formula (I) may be carried out in the presence of gaseous hydrogen and a catalyst such as Pd/C, Rh/C, Pt/C, Raney Nickel, and the like. Mixtures of catalysts may also be used. The reaction may be conducted in the presence of solvents such as methanol, dichloromethane, dioxane, acetic acid, ethyl acetate and the like. Mixtures of solvents may also be used. A pressure between atmospheric pressure to 100 psi may be employed. The catalyst may be 5-10% Pd/C and the amount of catalyst used may range from 50-300% w/w.

It is appreciated that in any of the above-mentioned reactions any reactive functional group in the substrate molecule may be protected according to the conventional chemical practice. Suitable protecting groups in any of these reactions are those used conventionally in the art, and the methods of formation and removal of such protecting groups are those conventional methods appropriate to the molecule being protected.

The invention is explained in detail in the example given below which is provided by way of illustration only and therefore should not be construed to limit the scope of the invention.

EXAMPLE

Synthesis of {4-[4-(2,4-Dioxothiazolidin-5-ylm-ethyl)phenoxy]-phenyl}acetic acid (Compound 1)

Step I: Synthesis of [4-(4-Formylphenoxy)phenyl]acetic acid

To a suspension of 4-hydroxyphenylacetic acid (5.8 g, 38.2 mmoles) in dry DMF (50 mL) under argon, was added $K_2CO_3$ (15.8 g, 114.5 mmoles), and 4-fluorobenzaldehyde (23.7 g, 190.8 mmoles), and the reaction mixture was stirred at 78±2° C. for 18 hours under argon (Note: the reaction mixture becomes very viscous soon after the addition of 4-fluorobenzaldehyde, which slowly liquefies again). Subsequently the reaction mixture was cooled to room temperature, then poured into water (250 mL) and stirred for 15 minutes. The aqueous layer was extracted with ethyl acetate (2×75 mL); the organic layer was discarded and the resulting aqueous layer was acidified with HCl (~6M) to pH 2.0. The aqueous layer was extracted with ethyl acetate (2×100 mL), the combined organic layers were washed with brine (50 mL), dried over anhydrous magnesium sulfate and evaporated under reduced pressure to afford a mixture which was purified by silica gel chromatography using hexane-ethyl acetate (7:3) containing 1% acetic acid as eluent to yield a pale yellow solid (2.5 g, 25.6%). $^1$H NMR (400 MHz, DMSO-$d_6$): δ ppm: 12.34 (br,

1H), 9.92 (s, 1H), 7.92 (d, J=8.8 Hz, 2H), 7.35 (d, J=8.8 Hz, 2H), 7.11 (overlapped d, J=8.8 Hz, 2H), 7.10 (overlapped d, J=8.8 Hz, 2H), 3.61 (s, 2H).

Step II: Synthesis of {4-[4-(2,4-Dioxothiazolidin-5-ylidenemethyl)phenoxy]phenyl}acetic acid The aldehyde from the Step I (2.22 g, 8.67 mmoles) was dissolved in toluene (30 mL), and benzoic acid (0.16 g, 1.30 mmoles), piperidine (0.096 g, 1.13 mM) and 2,4-thiazolidinedione (1.22 g, 10.40 mmoles) were added sequentially to it. Water was azeotropically removed from the above reaction mixture for about 2 hours. Subsequently the reaction mixture was cooled to room temperature, and filtered. The pale yellow solid, which separated out, was boiled in ethyl acetate (50 mL) for 5 minutes, cooled and filtered. This procedure was repeated once again to yield the product 2.63 g, 85.4%. $^1$H NMR (MHz, DMSO-$d_6$) δ ppm: 12.42 (br, 1H), 7.64 (s, 1H), 7.59 (d, J=8.4 Hz, 2H), 7.32 (d, J=8.8 Hz, 2H), 7.08 (d, J=8.8 Hz, 2H), 7.05 (J=8.8 Hz, 2H), 3.58 (s, 2H).

Step III: Synthesis of {4-[4-(2,4-Dioxothiazolidin-5-ylmethyl)phenoxy]phenyl}acetic acid Palladium on carbon (10%, 0.5 g), ammonium formate (3.55 g, 56.34 mmol) and the Step II material (1.0 g, 2.82 mmol) were sequentially added to acetic acid (10 mL) under an inert atmosphere and the reaction mixture was refluxed for 15 hours. Since the reaction was still incomplete after 15 hours, palladium on carbon (10%, 0.5 g), and ammonium formate (3.55 g, 56.34 mmol) were re-added and the reaction was refluxed for an additional 15 hours. Subsequently the reaction mixture was cooled to room temperature, and filtered through a Celite® bed. The bed was washed thoroughly with ethyl acetate (2×50 mL), and the solvent evaporated. Purification of the residue by silica gel chromatography, using hexane-ethyl acetate (3:2) mixture containing acetic acid (1%) afforded the desired compound. Yield: 0.52 g, 52%. m.p. 166° C. $^1$H NMR (MHz, DMSO-$d_6$) δ ppm: 12.28 (br, 1H), 12.05 (br, 1H), 7.26 (overlapped d, J=8.8 Hz, 2H), 7.25 (overlapped d, J=8.8 Hz, 2H), 6.94 (overlapped d, J=8.8 Hz, 2H), 6.93 (J=8.8 Hz, 2H), 4.90 (dd, J=9.6 and 4.4 Hz, 1H), 3.55 (s, 2H), 3.36 (dd, 14.4 and 4.8 Hz, 1H) and 3.11 (dd, 14.4 and 9.2 Hz, 1H); MS m/z 356 [M-1]. The disodium salt, Compound 2, is prepared by mixing Compound 1 with two equivalents of NaCl in solution and lyophilizing the mixture.

Biological Testing

Glucose Uptake

Figure 1:
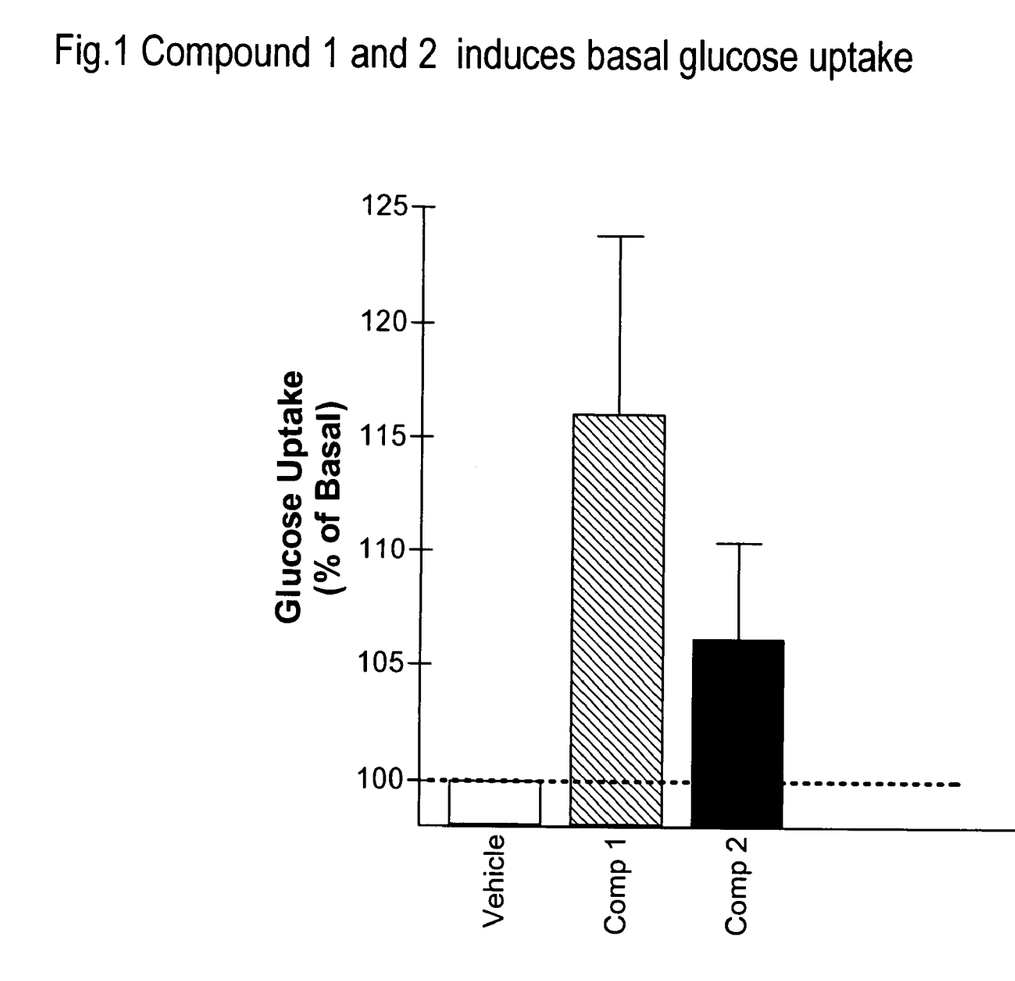
FIG. 1 is a graph of the results of the basal glucose uptake in 3T3-L1 adipocytes of Compounds 1 and 2 of the invention.

Referring to FIG. 1, 3T3-L1 fibroblasts were differentiated to adipocytes by a cocktail containing insulin, dexamethasone and IBMX for four days. Fully differentiated adipocytes were treated with the compounds (1.0 µM concentrations) or 0.1% DMSO for 72 hours and then glucose uptake was carried out for 10 minutes without any addition of insulin. Basal uptake was initiated by addition of radioactive $^{14}$C-2-deoxyglucose and after 10 minutes they were washed with cold PBS mixed with cold glucose. At the end, the cells were solubilized with 0.1% SDS and counted in a Beckman scintillation counter. Both the Compounds 1 and 2 induced glucose uptake over basal levels.

Cytotoxicity

Figure 2:
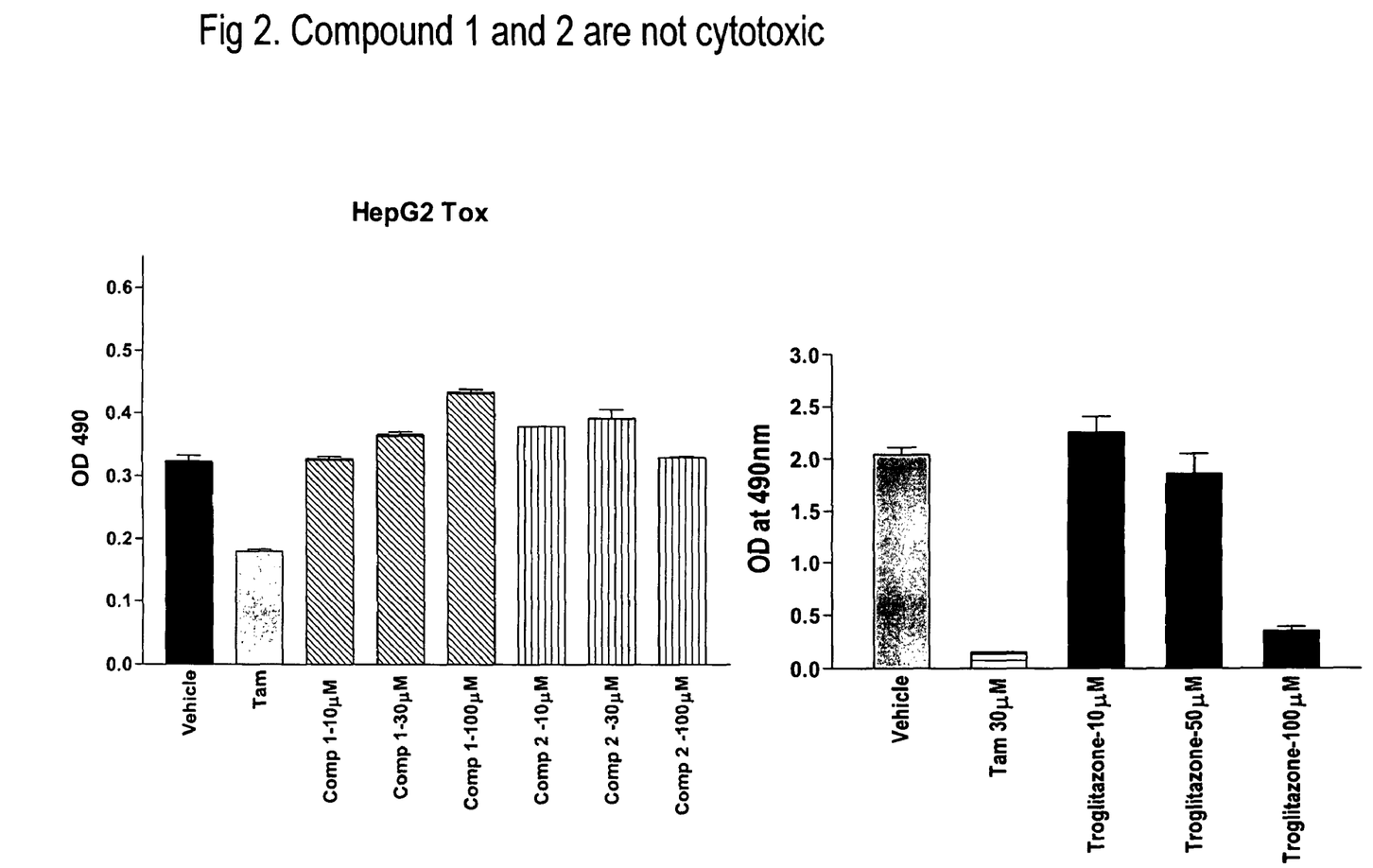
FIG. 2 shows the relative cytotoxicity of Compounds 1 and 2 compared to troglitazone (TZD).

Referring to FIG. 2, human liver cells (HepG2) are capable of metabolizing the drug substance as reported earlier. Troglitazone, the first marketed thiazolidinedione was withdrawn from the market because of severe hepatotoxicity. To find the cytotoxic effect of this class of new thiazolidinedione compounds (TZD), they were incubated in HepG2 cells for 24 hours and then the viability was measured by colorimetric reactions with MTS. Both Compounds 1 and 2 did not show any toxicity even at 100 µM concentrations.

Adipogenesis

Figure 3:
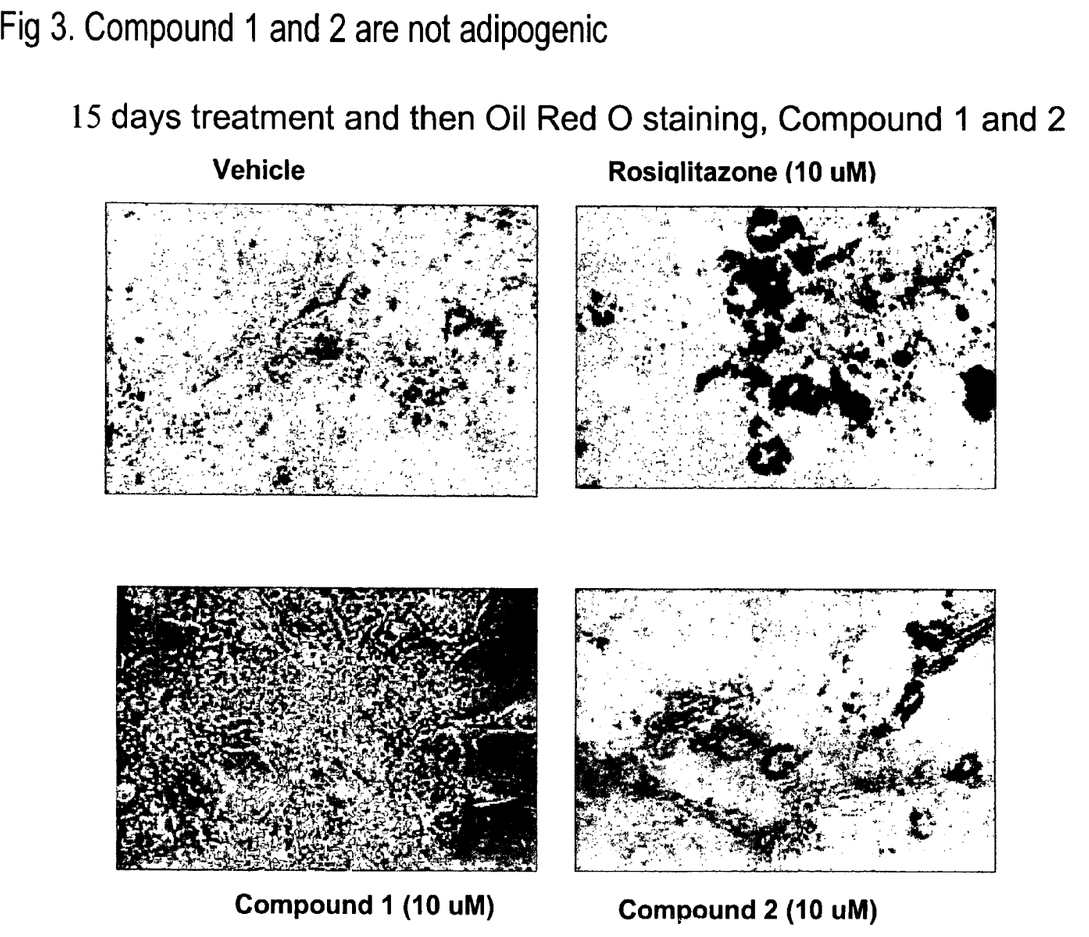
FIG. 3 shows microscopic images of stained fibroblasts comparing relative adipogenesis induced by rosiglitazone and compounds 1 and 2.

All known PPAR-γ agonists (both TZD or non-TZDs) induce differentiation in the fibroblast cells. The adipogenic potential of these compounds are correlated with their affinity to this receptor. Referring to FIG. 3, to check whether the Compounds 1 and 2 have any affinity to these receptors, 3T3-L1 fibroblasts were treated with either DMSO control or rosiglitazone (all at 10 µM concentrations) as positive control or these two compounds for several days at different concentrations. On day 11$^{th}$, the differentiated adipocytes were stained with Oil-red-O (Sigma) and washed thoroughly to remove the unbound stain. The stained differentiated adipocytes were visualized under high-resolution microscope. PPAR-γ agonist rosiglitazone strongly induced adipogenesis in this cell system whereas both compounds 1 and 2 remained unchanged, that is they are non-adipogenic and probably they do not.

Blood Glucose Lowering and Body Weight

Figure 4:
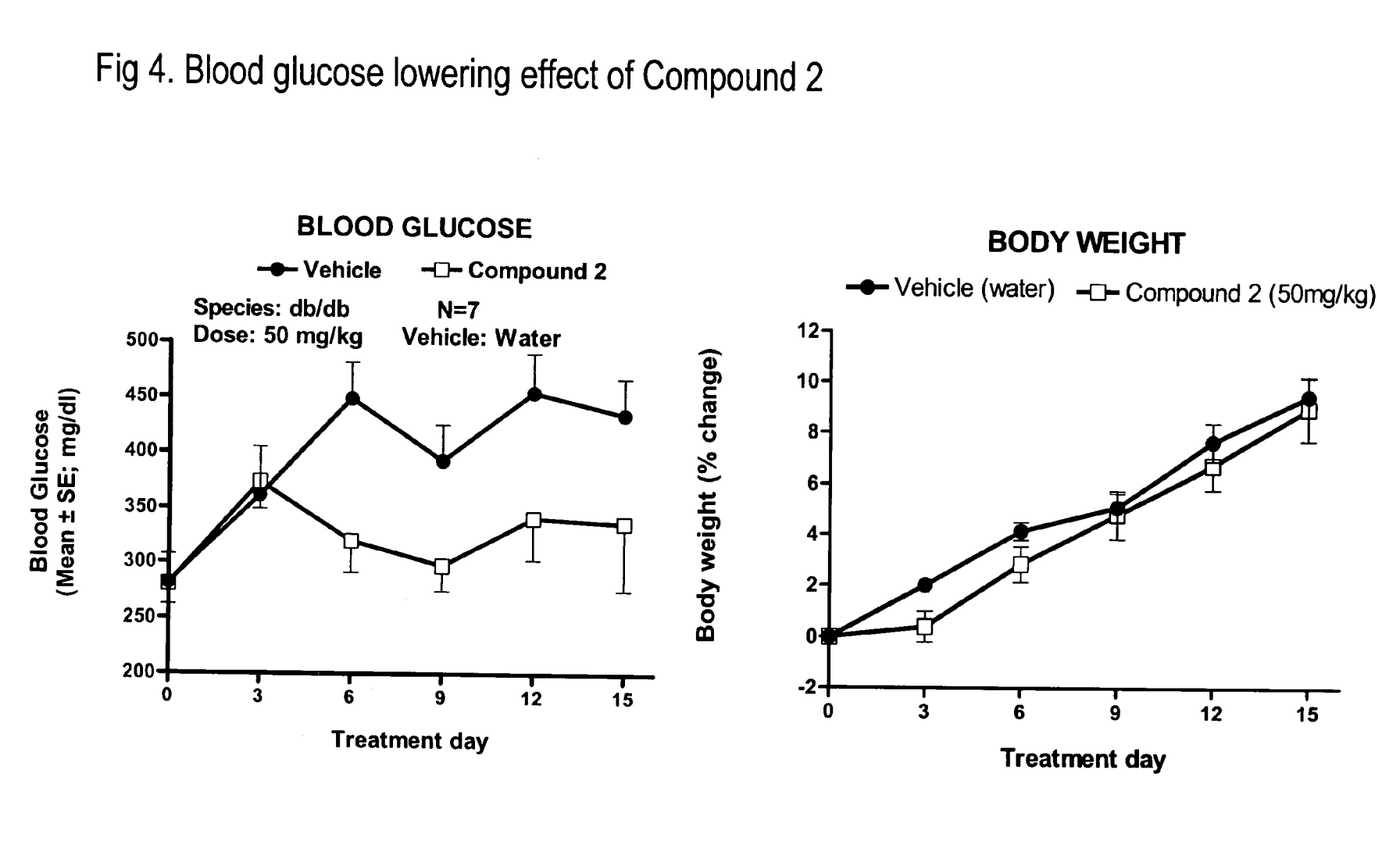
FIG. 4 shows the blood glucose lowering effect and effect on body weight from oral treatment of diabetic mice with Compound 2.

Referring to FIG. 4, ten week old male db/db (spontaneous model) diabetic mice were orally treated with compound 1 at a dose of 50 mg/kg body weight and blood glucose was monitored by one touch glucometer every day morning before the next dose.

Glucose Tolerance

Figure 5:
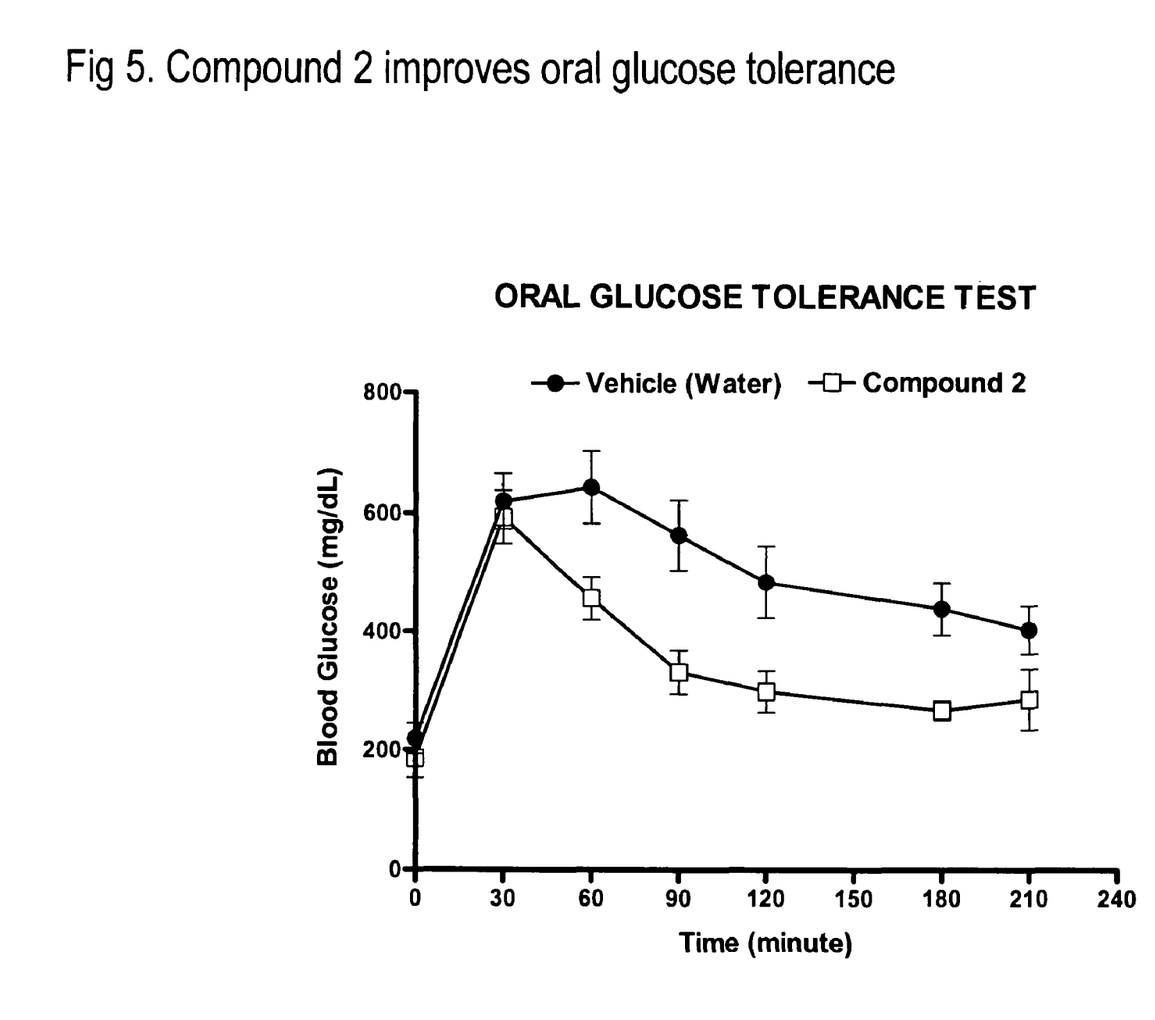
FIG. 5 shows the glucose tolerance in diabetic mice from oral administration of Compound 2.

Referring to FIG. 5, db/db mice (6-8 weeks old) were treated with Compound 2 (50 mg/kg) once daily for 14 days. On day 14 the animals were fasted overnight and gavaged with Compound 2, one hour prior to oral glucose challenge (2 g/kg BW). Blood glucose levels were monitored pre-dose, at 30, 60, 90, 120, 180 and 210 minutes, and showed improvement in glucose tolerance.

Serum Cholesterol

Figure 6:
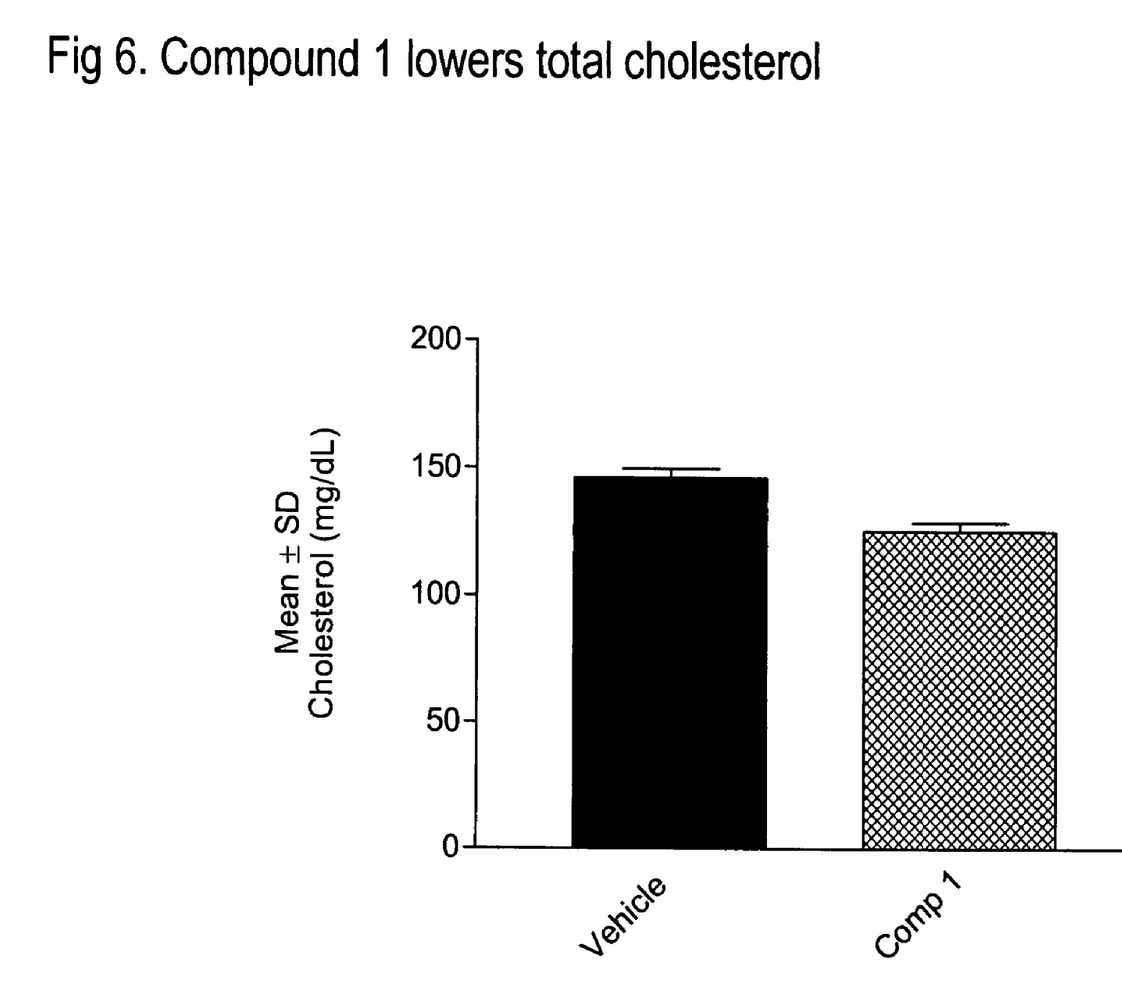
FIG. 6 shows the serum cholesterol lowering effect of Compound 1 in diabetic mice.

Referring to FIG. 6, db/db mice (6-8 weeks old) were treated with Compound 2 (50 mg/kg) once daily for 14 days. At the end of the study serum cholesterol was measured by a calorimetric method.

TNFα Inhibition

Figure 7:
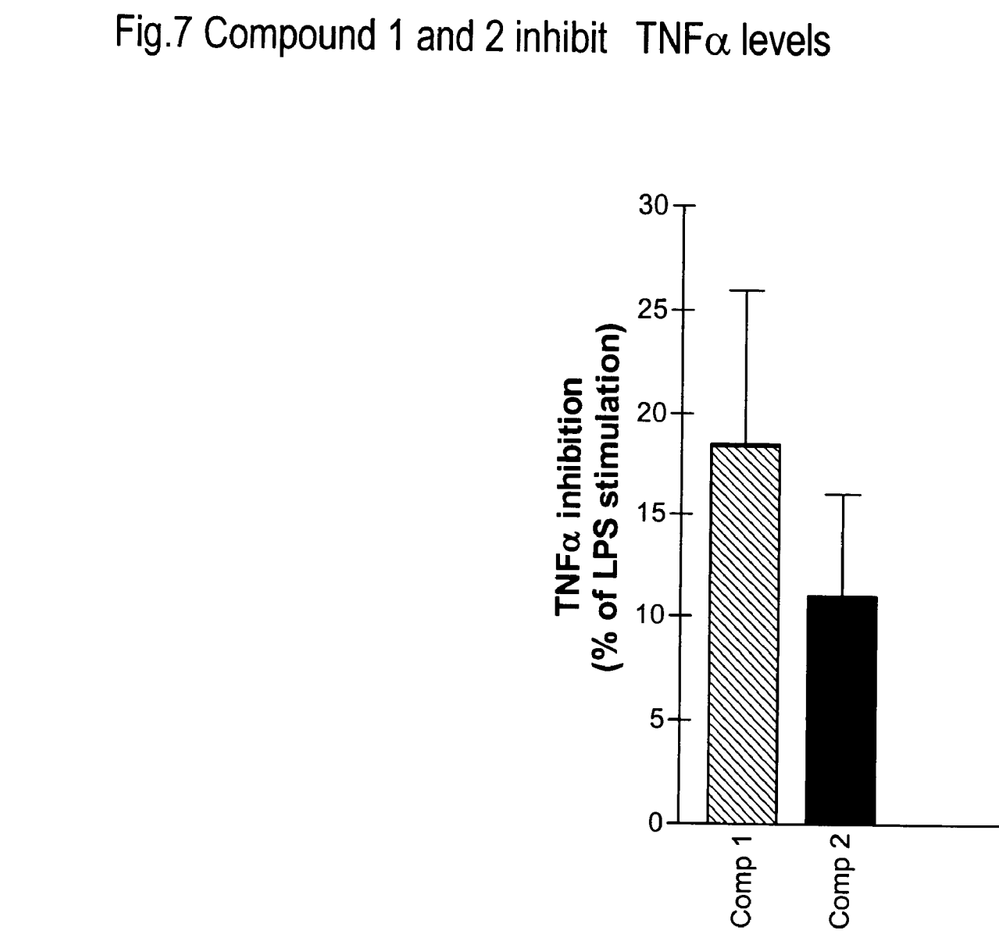
FIG. 7 shows the TNFα inhibition effects in human peripheral blood cells by Compounds 1 and 2.

Compound 1 and 2 inhibit major pro-inflammatory cytokines in human peripheral blood mononuclear cells isolated from volunteers. Referring to FIG. 7, human PBMC cells were cultured and incubated with Compound 1 and 2 at 10 μM concentration. Cells (1×10$^6$/mL) were challenged with lipopolysaccharides (LPS) at a concentration of (100 ng/mL) for 20 hours. TNF was measured by ELISA.

Inhibition of LPS-Induced NO Production

Figure 8:
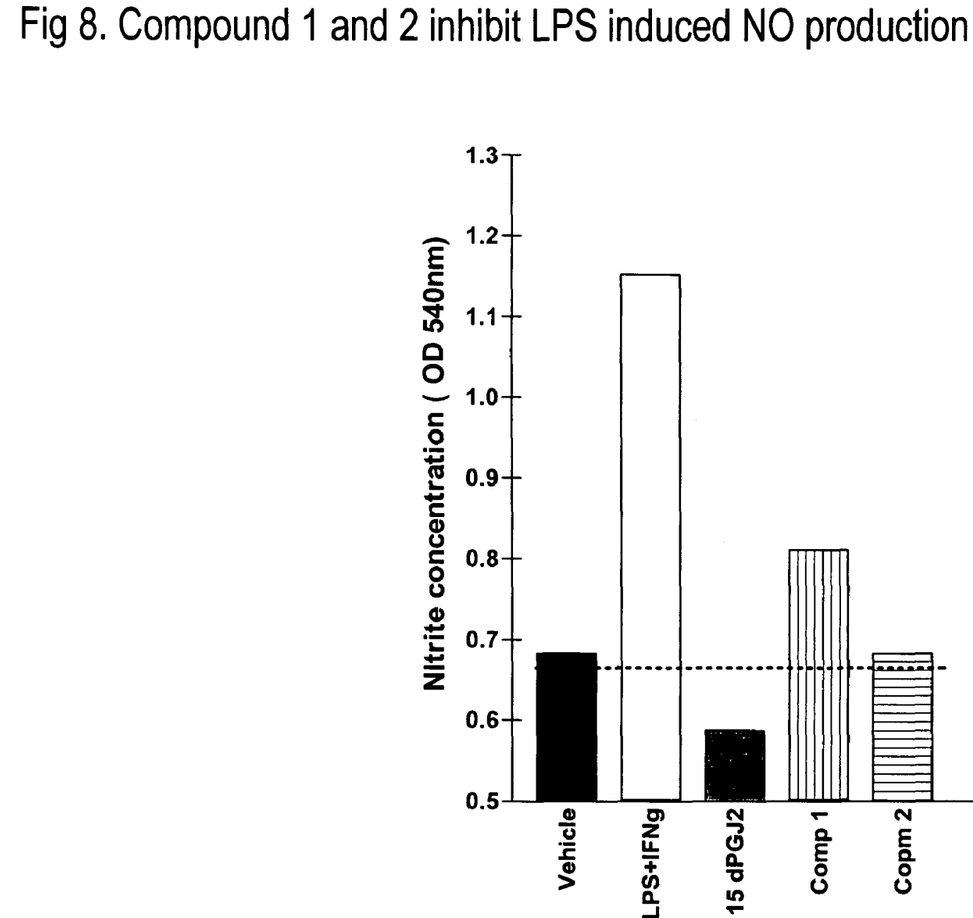
FIG. 8 shows the inhibition of LPS-induced NO production (by measurement of nitrite concentration) in mouse macrophages by Compounds 1 and 2.

Mouse macrophages (RAW 264.7) were plated in 6-well plate (2 million cells/well), and incubated at 37° C. with LPS (200 ng/mL+IFN-γ 10 U/mL) for 18 hours. Nitrite levels were measured by the Griess reagent. The results are shown in FIG. 8. All of the compounds were tested at 30 μM concentrations.

The invention claimed is:

1. A compound of the formula (I)

and tautomeric forms, stereoisomers, and pharmaceutically acceptable salts thereof, wherein ---- represents an optional bond; V represents CH or N; Y represents O or S; W represents O or $NR_8$; $R_8$ is selected from hydrogen or linear, branched, substituted or unsubstituted ($C_1$-$C_6$) alkyl groups; X represents $CR_9$, O or S wherein $R_9$ is hydrogen or $R_9$ together with Z forms a 5 or 6-membered aromatic or heteroaromatic ring system containing 1 to 2 heteroatoms selected from O, S or N; Z represents O, S or together with $R_9$ forms a 5 to 6 membered aromatic or heteroaromatic ring system containing 1 to 2 hetero atoms selected from O, S or N; $R_1$ and $R_2$ may be same or different and are independently selected from hydrogen, a halogen, hydroxy, nitro, cyano, formyl, $COR_{10}$ or linear or branched ($C_1$-$C_6$) alkyl group; or substituted or unsubstituted ($C_1$-$C_6$) alkoxy group; with the proviso that when one of $R_1$ and $R_2$ is hydrogen, the other is $COR_{10}$; $R_{10}$ represents —$OR_{11}$ or $NR_{12}R_{13}$; where $R_{11}$ represents hydrogen, a substituted or unsubstituted group selected from alkyl, alkenyl, aryl, aralkyl, heteroaryl, or a counter ion; $R_{12}$ and $R_{13}$ may be same or different and independently represent H or substituted or unsubstituted alkyl, alkenyl or aryl groups; or $R_{12}$ and $R_{13}$ together form a heteroaliphatic or heteroaromatic ring; $R_3$, $R_4$, $R_5$ and $R_6$, are selected from hydrogen, halogen; hydroxy, nitro, cyano, formyl, amino, linear or branched, substituted or unsubstituted ($C_1$-$C_6$) alkyl or alkoxy groups; haloalkyl groups, carboxylic acid and its esters and amides; unsubstituted sulfonamide, sulfonyl methyl group; $R_7$ represents hydrogen, substituted or unsubstituted alkyl, alkenyl, —$CH_2COOR$, aryl groups, or a counter ion; where R represents H or ($C_1$-$C_6$) alkyl group.

2. A compound according to claim 1, tautomeric forms, stereoisomers, and pharmaceutically acceptable salts thereof, wherein Y is O; X is S or $CR_9$; $R_1$ is $COR_{10}$ and $R_2$ is hydrogen or alkyl.

3. A compound according to claim 2, tautomeric forms, stereoisomers, and pharmaceutically acceptable salts thereof, wherein $R_3$ is hydrogen or halo; $R_4$ and $R_6$ are hydrogen; $R_5$ is hydrogen, halo, haloalkyl or alkoxy; and $R_7$ is hydrogen, —$CH_2COOR$ or a counterion.

4. A compound according to claim 3, tautomeric forms, stereoisomers, and pharmaceutically acceptable salts thereof, wherein V is CH; X is S; Y, Z and W are O; $R_{10}$ is —$OR_{11}$; $R_{11}$ is hydrogen or a counterion; $R_2$, $R_3$, $R_4$, $R_5$ and $R_6$ are hydrogen; and $R_7$ is hydrogen or a counterion.

5. A compound according to claim 3, tautomeric forms, stereoisomers, and pharmaceutically acceptable salts thereof, selected from:

{4-[4-(2,4-Dioxo-thiazolidin-5-ylmethyl)-phenoxy]-phenyl}-acetic acid;

{4-[4-(2,4-Dioxo-thiazolidin-5-ylmethyl)-phenoxy]-phenyl}-acetic acid disodium salt;

{4-[4-(4-Oxo-2-thioxo-thiazolidin-5-ylmethyl)-phenoxy]-phenyl}-acetic acid;

{4-[4-(3-Carboxymethyl-4-oxo-2-thioxo-thiazolidin-5-ylmethyl)-phenoxy]-phenyl}-acetic acid;

{4-[4-(2,4-Dioxo-thiazolidin-5-ylmethyl)-2-fluoro-phenoxy]-phenyl}-acetic acid;

{4-[2-Chloro-4-(2,4-dioxo-thiazolidin-5-ylmethyl)-phenoxy]-phenyl}-acetic acid;

{4-[4-(2,4-Dioxo-thiazolidin-5-ylmethyl)-2-trifluoromethyl-phenoxy]-phenyl}-acetic acid;

{4-[4-(2,4-Dioxo-thiazolidin-5-ylmethyl)-2-methoxy-phenoxy]-phenyl}-acetic acid;

{4-[4-(2,4-Dioxo-thiazolidin-5-ylmethyl)-3-fluoro-phenoxy]-phenyl}-acetic acid;

{4-[4-(2,4-Dioxo-thiazolidin-5-ylidenemethyl)-phenoxy]-phenyl}-acetic acid;

{4-[4-(2,4-Dioxo-thiazolidin-5-ylidenemethyl)-2-trifluoromethyl-phenoxy]-phenyl}-acetic acid;

{4-[4-(4-Oxo-2-thioxo-thiazolidin-5-ylmethyl)-2-trifluoromethyl-phenoxy]-phenyl}-acetic acid;

{4-[4-(4-Oxo-2-thioxo-thiazolidin-5-ylidenemethyl)-phenoxy]-phenyl}-acetic acid;

{4-[4-(3-Carboxymethyl-4-oxo-2-thioxo-thiazolidin-5-ylidenemethyl)-phenoxy]-phenyl}-acetic acid;

{4-[4-(3-Carboxymethyl-4-oxo-2-thioxo-thiazolidin-5-ylmethyl)-3-fluoro-phenoxy]-phenyl}-acetic acid;

{6-[4-(2,4-Dioxo-thiazolidin-5-ylmethyl)-phenoxy]-pyridin-3-yl}-acetic acid;

{6-[4-(4-Oxo-2-thioxo-thiazolidin-5-ylmethyl)-phenoxy]-pyridin-3-yl}-acetic acid;

{6-[4-(3-Carboxymethyl-4-oxo-2-thioxo-thiazolidin-5-ylmethyl)-phenoxy]-pyridin-3-yl}-acetic acid;

{6-[4-(2-Oxo-2,3-dihydro-1H-indol-3-ylmethyl)-phenoxy]-pyridin-3-yl}-acetic acid;

{6-[4-(2-Oxo-2,3-dihydro-1H-indol-3-ylmethyl)-2-trifluoromethyl-phenoxy]-pyridin-3-yl}-acetic acid;

{4-[4-(2-Oxo-2,3-dihydro-1H-indol-3-ylmethyl)-2-trifluoromethyl-phenoxy]-phenyl}-acetic acid;

{14-[4-(2,4-Dioxo-thiazolidin-5-ylmethyl)-phenoxy]-2-fluoro-phenyl}-acetic acid;

2-{4-[4-(2,4-Dioxo-thiazolidin-5-ylmethyl)-phenoxy]-phenyl}-N,N-dimethyl-acetamide;

2-{4-[4-(2,4-Dioxo-thiazolidin-5-ylmethyl)-phenoxy]-phenyl}-acetamide;

5-{4-[4-(2-Oxo-2-piperazin-1-yl-ethyl)-phenoxy]-benzyl}-thiazolidine-2,4-dione;

5-{4-[4-(2-Morpholin-4-yl-2-oxo-ethyl)-phenoxy]-benzyl}-thiazolidine-2,4-dione;

2-{4-[4-(2,4-Dioxo-thiazolidin-5-ylmethyl)-phenoxy]-phenyl}-butyric acid;

(4-{[4-(2,4-Dioxo-thiazolidin-5-ylmethyl)-phenyl]-methyl-amino}-phenyl)-acetic acid; and 5-{4-[4-(2-Oxo-2-piperazin-1-yl-ethyl)-phenoxy]-3-trifluoromethyl-benzyl}-thiazolidine-2,4-dione.

6. The compound {4-[4-(2,4-dioxo-thiazolidin-5-ylmethyl)-phenoxy]-phenyl}-acetic acid.

7. A compound according to claim 1 wherein the said pharmaceutically acceptable salt is selected from the group consisting of a hydrochloride, hydrobromide, sulfate, besylate, sodium, potassium, calcium and magnesium salt.

8. A pharmaceutical composition comprising a therapeutically effective amount of a compound or a mixture of compounds, tautomeric forms, stereoisomers, or pharmaceutically acceptable salts thereof according to any one of claim 1 to 6 or 7 sufficient to reduce in a subject the plasma level of glucose, fatty acids, cholesterol or triglycerides and a pharmaceutically acceptable carrier, diluent, excipient or solvate.

9. A pharmaceutical composition comprising a therapeutically effective amount of a compound or a mixture of compounds, tautomeric forms, stereoisomers, or pharmaceutically acceptable salts thereof according to any one of claim 1 to 6 or 7 sufficient to treat obesity, or diabetes in a subject.

10. A pharmaceutical composition according to claim 8 in the form of a tablet, capsule, powder, syrup, aerosol or suspension.

11. A pharmaceutical composition according to claim 9 in the form of a tablet, capsule, powder, syrup, aerosol or suspension.

* * * * *